United States Patent
Elakkad

(10) Patent No.: US 9,326,997 B2
(45) Date of Patent: May 3, 2016

(54) COMPOSITION AND METHOD FOR TREATION OLIGOOVULATION, OLIGOMENORRHEA AND AMENORRHEA

(71) Applicant: Ahlam E. Elakkad, Kirkland, WA (US)

(72) Inventor: Ahlam E. Elakkad, Kirkland, WA (US)

( * ) Notice: Subject to any disclaimer, the term of this patent is extended or adjusted under 35 U.S.C. 154(b) by 0 days.

(21) Appl. No.: 13/573,553

(22) Filed: Sep. 24, 2012

(65) Prior Publication Data

US 2016/0038539 A1 Feb. 11, 2016

(51) Int. Cl.

| | |
|---|---|
| *A61K 31/00* | (2006.01) |
| *A61K 33/00* | (2006.01) |
| *A61K 33/34* | (2006.01) |
| *A61K 33/30* | (2006.01) |
| *A61K 31/07* | (2006.01) |
| *A61K 31/375* | (2006.01) |
| *A61K 31/593* | (2006.01) |
| *A61K 31/51* | (2006.01) |
| *A61K 31/525* | (2006.01) |
| *A61K 31/455* | (2006.01) |
| *A61K 31/197* | (2006.01) |
| *A61K 31/44* | (2006.01) |
| *A61K 31/4188* | (2006.01) |
| *A61K 31/519* | (2006.01) |
| *A61K 31/714* | (2006.01) |
| *A61K 33/06* | (2006.01) |
| *A61K 33/26* | (2006.01) |
| *A61K 33/18* | (2006.01) |
| *A61K 33/04* | (2006.01) |
| *A61K 33/32* | (2006.01) |
| *A61K 33/22* | (2006.01) |
| *A61K 31/14* | (2006.01) |
| *A61K 31/194* | (2006.01) |
| *A61K 31/198* | (2006.01) |

(52) U.S. Cl.
CPC .............. *A61K 33/34* (2013.01); *A61K 31/07* (2013.01); *A61K 31/14* (2013.01); *A61K 31/194* (2013.01); *A61K 31/197* (2013.01); *A61K 31/198* (2013.01); *A61K 31/375* (2013.01); *A61K 31/4188* (2013.01); *A61K 31/44* (2013.01); *A61K 31/455* (2013.01); *A61K 31/51* (2013.01); *A61K 31/519* (2013.01); *A61K 31/525* (2013.01); *A61K 31/593* (2013.01); *A61K 31/714* (2013.01); *A61K 33/04* (2013.01); *A61K 33/06* (2013.01); *A61K 33/18* (2013.01); *A61K 33/22* (2013.01); *A61K 33/26* (2013.01); *A61K 33/30* (2013.01); *A61K 33/32* (2013.01)

(58) Field of Classification Search
CPC .............................. A61K 31/00; A61K 33/00
USPC .................... 514/9.8, 10.5, 168, 905
See application file for complete search history.

(56) References Cited

U.S. PATENT DOCUMENTS

| | | | |
|---|---|---|---|
| 7,238,373 | B2 | 7/2007 | Meyrowitz |
| 7,371,389 | B2 | 5/2008 | Keefe et al. |
| 7,767,668 | B2 | 8/2010 | Nagi et al. |
| 8,383,165 | B1 * | 2/2013 | Andrews ...................... 424/725 |
| 2002/0155163 | A1 | 10/2002 | Benjamin et al. |
| 2004/0220152 | A1 * | 11/2004 | Ben-Maimon et al. ....... 514/170 |
| 2006/0246128 | A1 | 11/2006 | Nagi et al. |
| 2006/0280800 | A1 | 12/2006 | Nagi et al. |
| 2007/0021396 | A1 | 1/2007 | Gloger et al. |
| 2007/0098819 | A1 | 5/2007 | Thys-Jacobs |
| 2009/0263508 | A1 | 10/2009 | Thys-Jacobs |
| 2010/0189789 | A1 | 7/2010 | Nagi et al. |
| 2010/0279989 | A1 | 11/2010 | Gloger et al. |
| 2012/0028936 | A1 | 2/2012 | Gloger et al. |

* cited by examiner

*Primary Examiner* — Brian-Yong Kwon
*Assistant Examiner* — Kyung Sook Chang

(57) ABSTRACT

A kit for treating Oligoovulation and/or Oligomenorrhea and/or Amenorrhea comprising a menstruation inducing composition comprising effective amounts of Vitamin A, Vitamin C, Vitamin D, Vitamin E, Vitamin B-1, Vitamin B-2, Vitamin B-3, Vitamin B-5, Vitamin B-6, Vitamin B-7, Vitamin B-9, Vitamin B-12, Iron, Iodine, Magnesium, Zinc, Selenium, Copper, Manganese, Chromium, Molybdenum, Boron, and Choline; and an ovulation regulating composition comprising effective amounts of calcium citrate, and magnesium citrate/aspartate.

3 Claims, No Drawings

COMPOSITION AND METHOD FOR TREATION OLIGOOVULATION, OLIGOMENORRHEA AND AMENORRHEA

FIELD OF THE INVENTION

The present invention relates to a composition and method treating Oligoovulation, Oligomenorrhea and Amenorrhea.

BACKGROUND OF INVENTION

Oligoovulation is typically defined as infrequent or irregular ovulation. During menstruation, follicles develop into eggs in the ovaries, in which normally, one egg matures faster and is released while the rest degenerate. Superovulation is when more than one follicle is developed into mature eggs. Oligomenorrhea is typically defined as infrequent, often light menstrual periods (intervals exceeding 35 days). Amenorrhea is the absence of a menstrual period in a woman of reproductive age. Oligoovulation, Oligomenorrhea and Amenorrhea are common in conditions such as PolyCystic Ovary Syndrome (PCOS), one of the most common female endocrine disorders. PCOS is a disorder in which eggs do not get released during ovulation. Instead of the follicle breaking open to release mature eggs immature follicles group together to form large cysts or lumps. The eggs mature within the follicles, but the follicles do no break open to release the mature eggs. PCOS produces oligoovulatory and oligomenorrheic symptoms in approximately 5% to 10% of women of reproductive age (12-45 years old). It is thought to be one of the leading causes of female subfertility and the most frequent endocrine problem in women of reproductive age. The symptoms and severity of the syndrome vary greatly among affected women.

There is no cure or treatment for PCOS. The medical field has many options for managing the symptoms of PCOS. The Management of polycystic ovary syndrome focuses on infertility, hirsutism, acne, and cardiovascular risks such as obesity, high blood cholesterol, diabetes, and high blood pressure.

For fertility and pregnancy, the medical field focuses on triggering ovulation by using an anti-estrogen medication such as Clomiphene alone or in combination with Metformin or injections of gonadotropins.

For regular menstruation without pregnancy, countering against endometrial cancer, the medical field would prescribe a low-dose contraceptives combined with synthetic estrogen and progesterone or an alternative approach of taking progesterone for 10 to 14 days each month to regular the menstrual cycle.

For insulin resistance, typically, the medical field would prescribe Metformin which is prescribed to treat Type 2 Diabetes and treating insulin resistance.

While Polycystic Ovarian Syndrome is the most common cause of female fertility, it is directly related to Type 2 Diabetes which is a metabolic disorder that occurs when there is an insulin disorder caused by either the pancreas not producing enough of the hormone insulin or the body stops responding to insulin. It is believed that high levels of insulin contribute to increased production of androgen which worsens the symptoms of PCOS. The medical field prescribes medications to reduce androgen levels and birth control pills to regulate menstruation; preventing further medical complications. Progestins and insulin sensitizing medications are prescribed to induce menstrual period and restoring normal cycles.

The last resort option of treating PCOS is a surgery called ovarian drilling to treaty PCOS which is a small incision to puncture the ovary and destroy small portion of the ovary to improve the hormone levels and ovulation.

In the treatment of controlling the symptoms of PCOS, Diet and exercise is often recommended to reduce the risk of developing diabetes and/or heart disease. Following a special diet is a vital aspect in PCOS care. Hence, managing blood sugar level via diet combined with moderate exercise can often help in reducing the response of insulin and improves insulin resistance.

Thus there is a present and continuing need for new emmenagogues for the treatment of Oligoovulation, Oligomenorrhea and Amenorrhea.

SUMMARY OF THE INVENTION

It is an object of the present invention to provide an emmenagogue for the treatment of Oligoovulation, Oligomenorrhea and Amenorrhea which eventually treats the side effect symptoms of obesity, infertility, hirsutism, acne, cardiovascular risks, and endometrial cancer. It is the objective to naturally induce ovulation produces the desired result of pregnancy and/or menstruation.

It is another object of the present invention to provide an inducing composition for the treatment of Oligoovulation and an emmenagogue for treating Oligomenorrhea, neither of which relies upon the use of hormonal therapy.

It is yet another object of the present invention to provide a method for treating Oligoovulation, Oligomenorrhea and Amenorrhea.

It is yet another objective of the present invention to regulate the menstruation to monthly repeated event on regular basis with a predicted schedule.

It is still yet another object of the present invention to provide a method for the treatment of Oligoovulation, Oligomenorrhea and Amenorrhea comprising two steps, wherein the first step is taking a specific nutritional supplement that induces ovulation, and, optionally, the second step is taking a second specific nutritional supplement that regulates the menstrual cycles to more than eight cycles a year.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DETAILED DESCRIPTION OF SPECIFIC EMBODIMENTS

The present invention is a composition and method treating/inducing Oligoovulation, eliminating Amenorrhea, and regulating Oligomenorrhea. The composition according to the present invention is a two part composition, an inducing composition and a regulating composition, each part of which is taken at a different interval from the other as discussed below.

The Inducing Composition

The first composition is an inducing composition that comprises a nutritional supplement used for inducing/generating/creating Oligoovulation. Table 1 illustrates the preferred composition and further illustrates variances in the compositional make up of the first composition.

beta-carotene. Beta-carotene features a built-in limiting mechanism since is not a preformed form of Vitamin A.

Vitamin C (as ascorbic acid) is a naturally occurring organic compound with antioxidant properties that protect the body against oxidative stress. It dissolves well in water to give mildly acidic solutions and, in solution, forms a "vitamer," of vitamin C. Because of its high solubility in water, the body does not store vitamin C. Vitamin C is needed for growth, repair of tissue, healing wounds, and repairing and maintaining bones and teeth and plays a major role in the synthesis of collagen, the main structural protein of joints, skin, bone, cartilage, tendons, ligaments, gums and blood vessels. Although only a few milligrams daily are necessary to prevent a deficiency disease (i.e. scurvy), much higher levels in divided doses help reap the full benefits of vitamin C's antioxidant properties. Further, vitamin C helps the body to absorb dietary iron. There has been research to indicate that vitamin C could help people with Type 2 Diabetes by maintaining glycemic control which is the measurement of glucose (blood sugar) level per consumption of carbohydrates. Hence, higher plasma vitamin C levels were shown to be associated with a substantially decreased risk of diabetes and may help in Type 2 Diabetes.

TABLE 1

| Component | Amount per Serving | | Lower Range | | Upper Range | |
|---|---|---|---|---|---|---|
| Vitamin A (100% as beta-Carotene) | 4500.00 | IU | 3300.00 | IU | 5000.00 | IU |
| Vitamin C (as Ascorbic Acid) | 120.00 | mg | 15.00 | mg | 1000.00 | mg |
| Vitamin D (as Cholecalciferol D-3) | 400.00 | IU | 400.00 | IU | 600.00 | IU |
| Vitamin E (as natural d-alpha Tocopheryl Succinate) | 30.00 | IU | 22.00 | IU | 30.00 | IU |
| Vitamin B-1 (as Thiamin Hydrochloride/Thiamin Mononitrate) | 1.40 | mg | 1.10 | mg | 1.50 | mg |
| Vitamin B-2 (as Riboflavin) | 1.60 | mg | 1.10 | mg | 1.60 | mg |
| Vitamin B-3 (as Niacinamide) | 18.00 | mg | 14.00 | mg | 35.00 | mg |
| Vitamin B-5 (as Calcium d-Pantothenate) | 7.00 | mg | 1.0 | mg | 7.0 | mg |
| Vitamin B-6 (as Pyridoxine Hydrochloride) | 10.00 | mg | 10.00 | mg | 25.00 | mg |
| Vitamin B-7 (as Biotin) | 35.00 | mcg | 30.00 | mcg | 70.00 | mcg |
| Vitamin B-9 (as Folic Acid) | 1000.00 | mcg | 400.00 | mcg | 1000.00 | mcg |
| Vitamin B-12 (as Cyanocobalamin) | 8.00 | mcg | 1.00 | mcg | 200.00 | mcg |
| Calcium (as Calcium Carbonate) | 600.00 | mg | 300.00 | mg | 1000.00 | mg |
| Iron (as Ferrous Fumarate) | 18.00 | mg | 10.0 | mg | 45.00 | mg |
| Iodine (as Potassium Iodide) | 290.00 | mcg | 150.00 | mcg | 1100.00 | mg |
| Magnesium (as Magnesium Oxide) | 200.00 | mg | 75.00 | mg | 350.00 | mcg |
| Zinc (as Zinc Oxide) | 15.00 | mg | 12.00 | mg | 20-25.0 | mg |
| Selenium (as Selenium Yeast) | 70.00 | mcg | 60.00 | mcg | 200.00 | mcg |
| Copper (as Copper Gluconate) | 1.30 | mg | 1-3.00 | mg | 8-10.00 | mg |
| Manganese (as Manganese Sulfate) | 2.60 | mg | 2.0 | mg | 11.0 | mg |
| Chromium (as Chromium Yeast) | 45.00 | mcg | 30.00 | mcg | 45.00 | mcg |
| Molybdenum (as Sodium Molybdate) | 50.00 | mg | 45.00 | mg | 50.00 | mg |
| Boron (as Boron Citrate) | 150.00 | mcg | 0.15 | mg | 3.00 | mg |
| Choline (as Choline Bitartrate) | 550.00 | mcg | 450.00 | mcg | 550.00 | mcg |

Vitamin A (as 100% beta-carotene). Beta-carotene is an important antioxidant and immune system booster. Beta-carotene is water-soluble. Beta-carotene can be stored in the liver and body fat and converted to retinal by the body only when needed by the body; thus making it a form of vitamin A. Vitamin A plays an essential role in vision, skin health, and immunity. For prenatal care, vitamin A is essential nutrient for normal cellular function, including reproduction and development. The risk during pregnancy is that too much of the preformed Vitamin A can lead to birth defects and liver toxicity while there is no risk of overdosing when consuming Vitamin D3 (as cholecalciferol) is both a fat-soluble vitamin and a hormone. It is converted in the liver to calcifediol then converted in the kidney to calcitriol, which is the active form of vitamin D. As a vitamin, cholecalciferol helps the body absorb calcium and metabolize phosphorus to create bone and aid in treating or preventing bone or skin conditions. As a hormone cholecalciferol is referred to as calcitrol and is a secosteroid that regulates bone mineralization and levels of calcium and phosphorus in the body. Vitamin D3 is essential for overall health, cardiovascular health, bone health, mental health, prevention of cancer, and immune system response. While vitamin D3 is produced in skin exposed to ultra violet rays, or is available through food sources, Cholecalciferol is an appropriate dietary source. There are indications that vitamin D3 plays an important role in glucose metabolism; hence, vitamin D3 may increase both insulin secretion and insulin sensitivity. As a consequence, vitamin D3 could be a factor in improving glucose tolerance or preventing development of Type 2 Diabetes. Vitamin D3 is important for PCOS sufferers because of its role in calcium absorption and regulation. Deficiency in vitamin D3 could contribute to insulin resistance.

Vitamin E (as d-alpha tocopheryl succinate) is a powerful antioxidant that is vital in maintaining heart health. Supplementation of vitamin E is important because dietary sources (e.g. almonds, pecans, and wheat germ oil) contain only small amounts. The vitamin E used in the nutritional supplement (d-alpha tocopherol) is absorbed at a higher rate than the synthetic form (dl-alpha tocopherol).

The medical field has recently made recommendations about the importance of B vitamins to sufferers from PCOS. Since B vitamins can help the liver process hormones, vitamin B6 helps with fertility issues, maintains normal balance, and in combination with B2 and B3, contributes to normal thyroid hormone production. B2, B3, B5 and B6 can control weight and blood sugar levels.

Vitamin B-1 (as Thiamin HCL/Thiamine mononitrate) plays a major role in converting carbohydrates from food into energy. It is also involved in maintaining muscular function, especially the heart. B-1 deficiency impairs the brain's ability to produce acetylcholine, a primary brain chemical involved in memory. Thiamine is water and helps the body convert food (carbohydrates) into fuel (glucose) and help metabolize fats and protein; hence producing energy. It is essential for proper physical and cognitive development. Thiamine is referred to as the "anti-stress" vitamin because it strengthens the immune system and improves the body's ability to withstand stressful conditions. Since it is water-soluble, Thiamine is expelled through urine, and therefore, must be consumed regularly.

Vitamin B-2 (as riboflavin) is an antioxidant that fights free radicals which damage cells and DNA, contribute to the aging process, and causes heart disease and cancer. It plays a critical role in converting food into energy and is involved in several enzymatic pathways. Intense exercise and oral contraceptives increase the need for riboflavin. Riboflavin deficiency contributes to fatigue, slowed growth, digestive problems, sores around the mouth, swollen magenta-colored tongue, and sensitiveness to light. Riboflavin is a water-soluble compound and needs to be replenished regularly.

Vitamin B-3 (as niacinamide) is involved in over 200 different reactions in the metabolism of carbohydrates, fat, and protein. Niacin also helps the body make various sex and stress-related hormones in the adrenal glands and improves circulation. Niacinamide is water-soluble and needs to be replenished regularly.

Vitamin B-5 (as calcium pantothenate) is water-soluable vitamin that is used in the synthesis of coenzyme A (CoA) as well as to synthesize and metabolize proteins, carbohydrates, and fats. Coenzyme A may act as an acyl group carrier to form acetyl-CoA and other related compounds; this is a way to transport carbon atoms within the cell. It is involved in releasing energy from dietary carbohydrates, synthesizing various hormones. Calcium pantothenate is often used in dietary supplements because, as a salt, it is more stable than pantothenic acid in the digestive tract, allowing for better absorption. As an alternative medicine, pantethine has been used to help lower cholesterol (serum) and triglycerides in diabetics. Vitamin B-5 is water-soluble and needs to be replenished regularly.

Vitamin B-6 (as pyridoxine HCL) is necessary for protein synthesis (i.e. muscle growth). Increased protein consumption raises B-6 requirements. It is also necessary for the production of serotonin, often called the "feel-good" hormone. Vitamin B-6, along with folic acid and vitamin B-12, are "heart healthy" because of their role in reducing homocysteine, an amino acid that promotes heart disease. Vitamin B-6 is a coenzyme and helps in metabolizing protein and carbohydrates, the production of insulin and red and white blood cells, and the synthesis of neurotransmitters, enzymes, and prostaglandins. Pyridoxine is often used as 'pyridoxine hydrochloride' which assists in balancing of sodium and potassium and promotion of red cell production. It is linked to cardiovascular health by decreasing the formation of homocysteine. Pyridoxine aids in balancing hormonal changes in women and strengthening the immune system. Deficiency of pyridoxine may cause anemia, nerve damage, seizures, skin problems, and sores in the mouth. It is necessary for proper nerve function and for metabolizing nutrients. The essential fatty acid linoleic acid requires this vitamin in order to be digested and assimilated, and release of glycogen from the liver occurs with the help of vitamin B6. Vitamin B6 is water-soluble and needs to be replenished regularly.

Vitamin B-7 (as Biotin) is best known for its role in cell growth, the production of fatty acids, and the metabolism of fats and amino acids. It plays a role in the citric acid cycle, which is the process by which biochemical energy is generated during aerobic respiration. Biotin is a coenzyme in the synthesis of fatty acids, isoleucine, and valine, and it plays a role in gluconeogenesis. Biotin not only assists in various metabolic reactions but also helps to transfer carbon dioxide. Biotin assists in the growth of hair, skin, nails, sexual organs, blood cells and bone marrow; and at a more basic level, biotin is necessary for gene replication. Biotin may also be helpful in maintaining a steady blood sugar level. Vitamin B-7 is water-soluble and needs to be replenished regularly.

Vitamin B-9 (as Folic Acid) is important for heart health due to its role in regulating homocysteine levels. Elevated homocysteine is linked to heart disease and Alzheimer's disease. Deficiency during early pregnancy significantly increases the risk for neural tube defects. Although folic acid is nontoxic, mega doses can mask an underlying vitamin B-12 deficiency. Folic acid is essential for bodily functions: to manufacture healthy red blood cells and prevent anemia; to synthesize DNA, repair DNA, and methylate DNA. It is important in aiding rapid cell division and growth in infancy and pregnancy. Folic acid is water-soluble and needs to be replenished regularly.

Vitamin B-12 (cyanocobalamin) contributes to normal functioning of the brain, nervous system, and formation of blood. Vitamin B12 deficiency can potentially cause severe and irreversible damage, especially to the brain and nervous system. Vitamin B12 deficiency may occur in certain health conditions (such as intestinal/stomach problems, poor nutrition, cancer, HIV infection, pregnancy, old age, alcoholism). Vitamin B-12 is water-soluble and needs to be replenished regularly.

Calcium (as calcium carbonate) is best known for its role in the development and maintenance of healthy bones and teeth, where 99% of it is stored. However, the remaining 1% of calcium in the blood is critical for proper muscle contraction, blood pressure regulation, and nerve function. Calcium binds with other minerals such as phosphate and aid in their removal from the body. The two main forms of calcium in supplements are carbonate and citrate. Calcium carbonate is absorbed most efficiently when taken with food, whereas calcium citrate is absorbed equally well when taken with or without food. Other calcium forms in supplements or fortified foods include gluconate, lactate, and phosphate. Calcium citrate malate is a well-absorbed form of calcium found in some fortified juices. Since in Type 2 Diabetes, the cells become resistant to the insulin effect, malfunction in its function of lowering blood sugar, calcium intake of 500 mg or more per day may have the effect of reducing risk of type 2 diabetes by improving the blood-sugar level and insulin performance.

Iron (as ferrous fumarate) plays an important role in biology, forming complexes with molecular oxygen in hemoglobin and myoglobin; these two compounds are common oxygen transport proteins in vertebrates. Hemoglobin, the protein in red blood cells carries oxygen through blood tissue and organs. Myoglobin, the protein that helps the muscles store oxygen, helps supply oxygen to muscles, and helps in enzymes that assist biochemical reactions. Iron is also the metal used at the active site of many important redox enzymes dealing with cellular respiration and oxidation and reduction in plants and animals. It is believed that iron may have a role in the pathogenesis of Type 2 Diabetes since it is a strong pro-oxidant. It is suggested that there is a positive association between high body iron stores which is measured by circulating ferritin level, and the risk of Type 2 Diabetes and of other insulin resistant states such as metabolic syndrome, gestational diabetes, and polycystic ovarian syndrome.

Iodine (from Potassium Iodide) is required for thyroid hormone synthesis. It is a trace mineral, meaning only small amounts are needed by the body. Normal thyroid function in fetuses and breastfed infants is crucial for normal neurocognitive development.

Magnesium (as magnesium oxide) is one of the most important minerals for health and helps activate over 300 enzyme systems in the body. Magnesium is vital for energy production and carbohydrate metabolism and is important for normal functioning of cells, nerves, muscles, bones, and heart. Magnesium helps to regulate insulin and blood sugar levels during pregnancy. It helps build and repair tissue and influences calcium metabolism which build strong bones and teeth. Higher dosages of 400 mg per day have been used to treat diabetes. Magnesium plays an important role in blood sugar metabolism. In Type 2 Diabetes, when insulin resistance which is when the level of insulin supplied in the blood are not able to deliver glucose. Magnesium can improve insulin sensitivity whereas a decrease in insulin sensitivity is a factor in development of Type 2 Diabetes and PCOS.

Zinc (as zinc oxide) is an excellent immune system booster. Zinc is also needed for muscle growth, insulin function, vision, and taste perception. It supports prostate health and the body's ability to protect itself against heavy metal toxicity, such as cadmium and lead.

Selenium (as Selenium Yeast) is an essential trace element that is a powerful antioxidant which significantly increases the effectiveness of vitamin E. It also contains antiviral properties and plays an important role in prostate, lung, and breast health. Selenium helps protect against heavy metal toxicity, especially mercury. Selenium preserve elasticity in body tissues, slows the aging process, improve oxygen flow to the heart, and help prevent abnormal blood clotting. Selenium may also play a role in normal growth, development, and fertility.

Copper (as Copper Gluconate) is a trace mineral. Copper Gluconate is a form of copper which can be absorbed readily. Copper is called "Brain food" which stimulates the brain. It is important for nerve function, bone growth, and help the body use iron and sugar. Copper deficiency could lead to anemia and osteoporosis. In addition, copper is important in the formation of hemoglobin which has a role in transporting oxygen throughout the body, myelin which is an insulating layer around the nerves produced in the fourteenth week of fetal development, melanin which creates pigmentation in eyes, hair, and skin, and collagen which determines the integrity of bones, skin, cartilage, and tendons, is copper dependent.

Manganese (as manganese Sulfate) is involved in chemical processes in the body, including processing of cholesterol, carbohydrates, and protein. In addition, is involved in many enzyme systems and acts as a co-factor for enzymes necessary for energy production, fatty acid synthesis, glucose metabolism, DNA and RNA synthesis, and the stimulation of glycogen storage in the liver, protein digestion, and cholesterol. Manganese is necessary for growth, maintenance of the nervous system, the development and maintenance of healthy bones and joints, the formation of blood clotting factors, female sex hormone function and thyroid hormone function. Deficiency in manganese causes impaired glucose tolerance (IGT) which is known as pre-diabetes which is when the blood sugar level is elevated; however, not to a diabetes. Manganese does have a role in regulating blood sugar, carbohydrate metabolism.

Chromium (as Chromium Yeast) is a supercritical mineral that is vital for blood sugar balance and carbohydrate metabolism. Chromium plays a role in how insulin helps the body regulate blood sugar levels. It may help people with diabetes lower blood sugar levels and a way of improving lean muscle and reducing body fat. Chromium is an insulin potentiator which prevents diabetes by improving insulin sensitivity. Chromium is important for PCOS sufferers because it helps in formation of glucose tolerance factor, which is released by the liver and is required in making insulin uptake more efficient in the body. Deficiency in chromium can lead to insulin resistance.

Molybdenum (as Sodium Molybdate) is an essential trace mineral that is required for several enzymatic reactions in the body. It functions as a cofactor for three enzymes: sulfite oxidase (which metabolize sulfur containing amino acids), Xanthine oxidase (which contributes to plasma antioxidant capacity of the blood), and aldehyde oxidase (which plays a role in metabolizing drugs and toxins).

Boron (as Boron Citrate) is an overlooked mineral essential for bone health. It reduces urinary loss of calcium. It helps the body process vitamin D and assist the body in using calcium and other minerals.

Choline (as Choline Bitartrate) is essential nutrient needed by the nervous system to produce neurotransmitter acetylcholine for memory and concentration. Choline also provides structure to cell walls and assists in converting carbohydrates to fat. It is helpful in producing hormones which enhance sexual, bladder, kidney, pancreatic, and liver function. Choline bitrate enhances athletic performance, reduces cholesterol levels, protects the liver from fat build up, lowers blood pressure, controls mood swings, and improves memory.

The inducing composition is in compliance with prenatal safety in both dosage and form. If the inducing composition succeeds in producing ovulation and pregnancy occurs, there is no need to terminate taking the composition, because it is composed of formulated multivitamins that make up many of the nutritional deficiencies in a mother's diet as well as being within the safe range for prenatal care.

The main objective of the inducer agent is to induce ovulation followed by menstruation. The recommended dosage is two tablets daily.

The Regulating Composition

The second composition is the regulating composition. Table 2 illustrates the preferred composition and further illustrates variances in the compositional make up of the regulating composition.

TABLE 2

| Component | Amount per two tablespoons | Lower Range | Upper Range |
|---|---|---|---|
| Calcium Citrate | 1200 mg | 1000 mg | 4000 mg |
| Magnesium Citrate/Aspartate | 600 mg | 300 mg | 1000 mg |
| Vitamin $D_3$ (cholecalciferol) | 800 IU | 300 IU | 1000 IU |

It is important for the calcium in the regulating composition be calcium citrate. Calcium carbonate is alkaline based while calcium citrate is acid based. Calcium is best absorbed when it is in an acidic environment. Calcium citrate does not require extra acids from a user's stomachs. Thus, users may take calcium citrate supplements any time of the day. Further, since the regulating composition is a slightly acidic composition, the solubility of calcium citrate is increased, hereby making more dissolved calcium available to the body.

It is important for the magnesium in the regulating composition be magnesium citrate/aspartate. Magnesium citrate is an ionic compound of magnesium and an organic citrate anion. Magnesium oxide is an ionic compound of magnesium and inorganic oxide anion. Thus, users may take magnesium citrate/aspartate supplements any time of the day. Further, since the regulating composition is a slightly acidic composition, the solubility of magnesium citrate is increased, hereby making more dissolved magnesium available to the body.

Preferably, the regulating composition is provided in water with flavorings added.

The main objective of the regulating agent is to regulate cycling to a monthly event with a predictable schedule and treat PCOS infrequent or usually eight or fewer menstruation cycles a year. The recommended dosage to produce such results has a dose of ¼ teaspoon taken after 48 hours of cycling every day for five days at the same time. In order to change the cycle length (number of days of blood flow) and/or possible release of more than one egg in a given month, the recommended dose is ¾ to 1 teaspoon. For immediate menstruation termination and/or reset of cycle schedule to a different date and/or remission of cystic conditions, the recommended dose is between 1 to 2 tablespoons.

In the method according to the present invention, a user takes a daily dose of the inducing composition, typically two tablets separated by 12 hours (a tablet in the morning and a tablet in the evening). The daily dose of the inducing composition induces ovulation followed by a menstruation cycle, with irregular cycle duration of the body, which averages between 28 and 41 days.

Taking less than the recommended dosage and/or irregularity of taking the inducing composition induces menstruation that varies from once a quarter to once every six months or no menstruation. Irregular intake of the inducing agent had no impact as long as a full daily dose was consumed within 24 hours of the missed dose.

The value of the inducing composition is in inducing ovulation, which produces menstruation events. Compare this with birth control pills, which induce menstruation without ovulation. Thus, the inducing composition produces the desired objective of ovulation.

Based on the intake dosage, the regulating composition will reset the date of the schedule and/or regulate the period to monthly cycles. Also based on the dosage of the regulating composition, the cycle was reduced from seven days to five days or three days and induced maturity/release of more than one egg.

Method of intake, the user takes a maximum of ¼ teaspoon dose (which will have the dosage measurement as described in table 2) of the regulating composition on the same day every day for five consecutive days to yield monthly cycles. The first dose must be taken after 48 hours of menstruation. Menstruation is calculated when the menstrual cycle first begins. Dosages small than the preferred dosages impair the effectiveness of regulating the cycle. Irregular intake of the regulating composition affects the menstruation start date, schedule, regularity, and duration.

Even though as a calcium supplement, the dosage is 2 tablespoon per day, taking more than 1 tablespoon of the recommended dosage could immediately stop menstruation and stops ovulation (followed by months of no cycles.). It is thought that over dosage of the regulating composition mirrors an Insulin Resistant Situation. With Insulin Resistant Situation, the shell around the ovaries get tough and hard and the egg can't burst out of the shell; hence, producing a cyst instead. Once a user takes too much of regulating composition, and the period terminates, and the user can restart ovulation by taking the inducing composition and reset the cycling schedule to a different date.

If the user takes the inducing composition and does not take the regulating composition, the menstruation date is extended to 30-40 days or per what is regular/normal per a woman's body. Women with PCOS don't ovulate, or ovulate infrequently, so they usually have eight or fewer cycles a year.

If the user takes the regulating composition and does not take the inducing composition, there is no impact on menstruation or ovulation.

Ovulating of more than one egg happens when while taking the inducing agent, the user takes the recommended dosage of ¾ to 1 teaspoon of the regulating agent five days before menstruation happens and while menstruation for five days, a total of 10 days.

If the user stops taking the regulating agent while still taking the inducing agent, the first month following the stop is regular (within 30 days), the 2nd and/or 3rd months after, menstruation period resets to regular irregular norms of every 30-40+ days and irregular repeats. Thus, it stretches out the period between the repeats. Which means, the PCOS's ovulate infrequently condition is in remission.

Intake of the regulator within ¾ teaspoon to 1 teaspoon for no longer than five days while not menstruating could cause spotting; however, the next month's cycle could be reduced from seven days to five days. It has the same effect while menstruating; although could have the side effect of either lighter blood flow or termination of the blood flow. In such case, during menstruation, it is preferable to wait until the third day (72 hours) before you start such dosage.

While still continuing the intake of the inducer, to immediately terminate menstruation during while bleeding/cycling, take 1 to 2 tablespoon per day. You will notice that immediately within 24 hours, if not within the hour, menstruation has terminated. Continuous intake of such high dosage of 1 to 2 tablespoon daily for no longer than 10 to 15 days will reset the cycling schedule to a different date for next month's cycle.

When you first start the treatment of inducing/regulating, it takes the body a minimum of three to six months to adjust and show results.

The preferred embodiment of the invention is described above in the Description of Preferred Embodiments including Table 1 on pages 5-6 and Table 2 on page 15. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A method for treating Oligoovulation or Oligomenorrhea or Amenorrhea comprising the steps of:
  a. Providing a menstruation inducing composition, wherein the menstruation inducing composition comprises an effective amount of each of the following: Vitamin A, Vitamin C, Vitamin D, Vitamin E, Vitamin B-1, Vitamin B-2, Vitamin B-3, Vitamin B-5, Vitamin B-6, Vitamin B-7, Vitamin B-9, Vitamin B-12, Calcium, Iron, Iodine, Magnesium, Zinc, Selenium, Copper, Manganese, Chromium, Molybdenum, Boron, and Choline,
  b. Providing an ovulation regulating composition, wherein the ovulation regulation composition comprises an effective amount of each of the following: Calcium Citrate and Magnesium Citrate/Aspartate,
  c. Having a user take the menstruation inducing composition on a daily basis, and
  d. Having the user take the ovulation regulating composition beginning at the onset of menstruation.

2. The method according to claim 1, wherein the menstruation inducing composition comprises:
  approximately amount per serving of each of 4500 IU Vitamin A, 120 mg Vitamin C, 400 IU Vitamin D, 30 IU Vitamin E, 1.40 mg Vitamin B-1, 1.60 mg Vitamin B-2, 18.00 mg Vitamin B-3, 7.00 mg Vitamin B-5, 10.00 mg Vitamin B-6, 35.00 mcg Vitamin B-7, 1000.00 mcg Vitamin B-9, 8.00 mcg Vitamin B-12, 600.00 mg Calcium, 18.00 mg Iron, 290.00 mcg Iodine, 200.00 mg Magnesium, 15.00 mg Zinc, 70.00 mcg Selenium, 1.30 mg Copper, 2.60 mg Manganese, 45.00 mcg Chromium, 50.00 mg Molybdenum, 150.00 mcg Boron, and 550.00 mcg Choline.

3. The method according to claim 1, wherein the ovulation regulation composition comprises:
  approximately amount per serving of each of 50.00 mg Calcium Citrate and 25.00 mg Magnesium Citrate/Aspartate.

* * * * *